United States Patent [19]

Sandhu

[11] Patent Number: 4,506,550

[45] Date of Patent: Mar. 26, 1985

[54] NON-DESTRUCTIVE TESTING SYSTEM EMPLOYING A LIQUID CRYSTAL DETECTOR CELL

[75] Inventor: Jaswinder S. Sandhu, Chicago, Ill.

[73] Assignee: Raj Technology Partnership, Chicago, Ill.

[21] Appl. No.: 399,997

[22] Filed: Jul. 20, 1982

Related U.S. Application Data

[63] Continuation-in-part of Ser. No. 232,247, Feb. 6, 1981, Pat. No. 4,379,408, which is a continuation-in-part of Ser. No. 224,173, Jan. 12, 1982, abandoned.

[51] Int. Cl.³ .................... G01N 29/00; G02F 1/11
[52] U.S. Cl. ........................................ 73/603; 350/330
[58] Field of Search .............. 73/603, 604, 606, 607, 73/655, 656; 350/330, 331 R, 334, 350; 367/7, 8, 10

[56] References Cited

U.S. PATENT DOCUMENTS

| | | | |
|---|---|---|---|
| 3,831,434 | 8/1974 | Greguss | 73/603 |
| 3,991,606 | 11/1976 | Dreyer | 73/603 |
| 4,338,821 | 7/1982 | Dion | 73/603 |

*Primary Examiner*—Stephen A. Kreitman

*Attorney, Agent, or Firm*—Hill, Van Santen, Steadman & Simpson

[57] ABSTRACT

There is disclosed herein an ultrasonic imaging system for use in non-destructively testing objects, which system includes a source of ultrasonic energy, a liquid crystal detector cell and an optical viewing system. The liquid crystal detector cell includes a pair of acoustically transmissive covers which encase a nematic liquid crystal material. The material exhibits an acousto-optic effect, and in particular, exhibits birefringence in response to ultrasonic energy. The cell construction, geometry, and material are acoustically matched to the frequencies of the insonifying ultrasonic transducer so as to optimize the performance of the cell. The covers are substantially acoustically transparent to ultrasonic energy incident on the cover at both normal and oblique attitudes. The acoustic impedance of the covers match as closely as possible to that of the coupling medium. The average alignment of the liquid crystal molecules, as indicated by the director, is selectively aligned to be oblique to the ultrasonic beam, and by reason thereof the cell exhibits high sensitivity and high image resolution in the "non-streaming" region. Electric field enhancement may be used to cooperate in aligning the liquid crystal molecules and to enhance the resolution and sensitivity of the image.

77 Claims, 7 Drawing Figures

FIG. 1
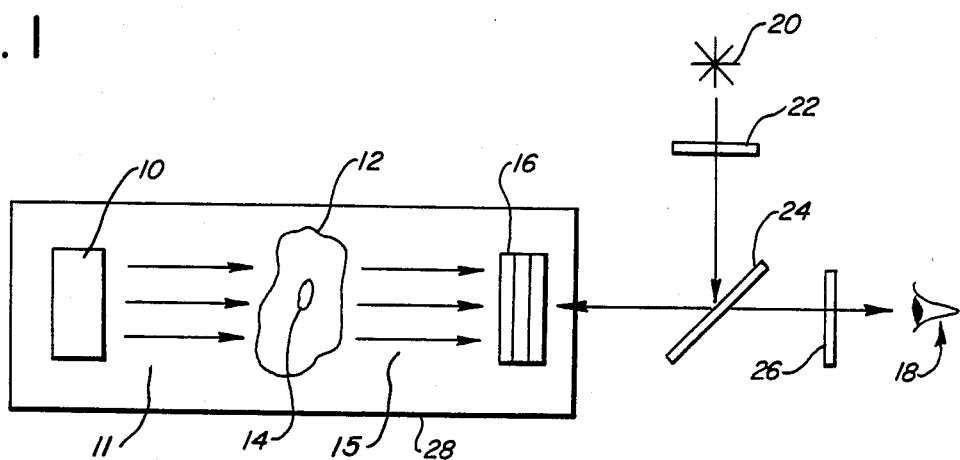
FIG. 2
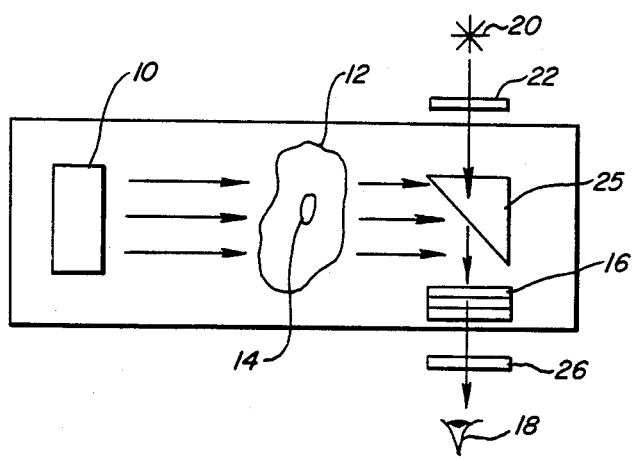
FIG. 7
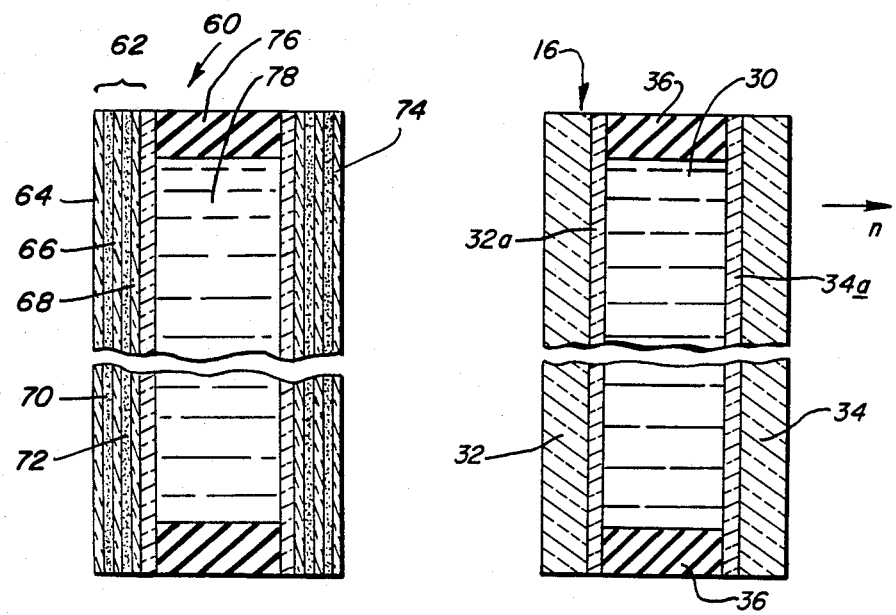
FIG. 3

NON-DESTRUCTIVE TESTING SYSTEM EMPLOYING A LIQUID CRYSTAL DETECTOR CELL

CROSS-REFERENCE TO RELATED APPLICATIONS

This application is a continuation-in-part of copending U.S. patent application, Ser. No. 232,247 filed on Feb. 6, 1981, now U.S. Pat. No. 4,379,408, which is a continuation-in-part of copending U.S. patent application, Ser. No. 224,173 filed Jan. 12, 1982, now abandoned.

BACKGROUND OF THE INVENTION

This invention relates to an apparatus and method for inspection and examination of bodies using ultrasonics, and more particularly, to an improved detector cell.

In many industrial and medical situations, it is desirable to examine the interior of a body for flaws or discontinuities. For example, industrially it is desirable to locate potential failure-initiating flaws and remove the product or part before it is used or to prevent its continued use. In medical situations, it is desirable to non-invasively examine internal organs and/or examine for tumors, etc. Presently ultrasound is used extensively in medicine to examine unborn fetus, tumors, etc.

One type of apparatus for ultrasonic non-destructive inspection is disclosed in U.S. Pat. No. 3,766,775 to Gunkel. Commerical ultrasonic inspection is based upon pulse-echo technology, whereby an ultrasonic signal or pulse is directed into a body, its echoes or reflections from the body are received and then electronically analyzed to establish an image. The images are then displayed using a cathode ray tube (CRT) or graphically plotted using an x-y plotter to develop what is referred to as an A-scan, B-scan or C-scan, etc.. Such an image will take a substantial length of time to develop, due to the considerable amount of time involved in scanning the body with the ultrasonic beam, this is particularly true if the body is large. Computers have been used to speed this process, but at the expense of sophisticated signal processing and cost. Furthermore, the images developed require a great deal of operator interpretation and operator skill to generate.

The equipment that is generally used in pulse-echo systems includes an ultrasonic transducer, complex signal processing equipment and complex image generating equipment. This equipment is large, does not easily lend itself to field use, and is not convenient for use in hand-held or hand-carried applications.

Proposals have been made in the past to use nematic liquid crystal materials as a detector in ultrasonic inspection systems. See, for example, U.S. Pat. No. to Dreyer, 3,597,043; Dreyer, U.S. Pat. No. 3,991,606; Kessler, et. al., U.S. Pat. No. 3,707,323; Greguss, U.S. Pat. No. 3,831,434.

Brenden, U.S. Pat. No. 3,879,989 uses cholesteric liquid crystals. For related art, also Kamei et al., U.S. Pat. No. 3,972,733; Wreford U. S. Pat. No. 3,137,837; Woodmansee U.S. Pat. No. 3,511,086 Sharpless U.S. Pat. No. 3,647,279; Mailer U.S. Pat. No. 3,837,423; Kamei et al. U.S. Pat. No. 3,972,733. A proposal to use an electro-optic system with liquid crystal display devices, and more particularly with a mixture of nematic and cholesteric liquid crystals, is disclosed in Cole, et. al., U.S. Pat. No. 3,984,343. See also publications by Bartolino et al., Jour. Appl. Physics, Vol. 46, No. 5, May 1975, p. 1928 et seq; Greguss, Acustica, Vol. 29 (1973), S. Hirzel Verlag, Stuttgart. p. 52 et seq; Nagai et al., Revue De Physique Appliquee, Vol. 12, No. 1 (January 1977) pp. 21–30.

If any of the patented or published systems had been successful, they would have eliminated the need for the complex signal processing and image forming equipment. However, the fact is that there are no commercially available ultrasonic inspection systems which provide an acceptable real time, liquid crystal, acousto-optical display. It is believed that none of the prior proposals has been capable of providing a commercially or medically acceptable image, and it is believed that none of the devices disclosed had acceptable perfomance characteristics such as sensitivity, contrast, response time, and resolution.

In my copending U.S. patent application, Ser. No. 232,247 filed Feb. 6, 1981, there is disclosed an improved ultrasonic imaging cell in which the ultrasonic signal from a body can be viewed directly and which includes a pair of cell covers, or substrates, with a nematic liquid crystal sealed therebetween. The cell covers are acoustically matched to their surrounding medium so as to minimize signal loss and so as to enhance the image. That application discloses laminated glass cell covers as a specific embodiment in which the thickness of the laminated layers is critically related to the wavelength of sound propagating therethrough.

The laminated structure of said co-pending application, Ser. No. 232,247 provides a siqnificant advance over the prior cell structures as disclosed in the Dreyer, Kessler, et. al., Greguss and Brenden prior art patents. However, the laminated structures require careful fabrication, and while they are functionally far superior to the existing prior art technology, it is desirable to provide a cell which is less expensive to fabricate and more easily fabricated, but which still has the desired acousto-optic properties.

Also, since filing my said co-pending application, Ser. No. 232,247, further research has led to significant discoveries that have permitted identification of factors that are, in my view, important to the production of an operative acousto-optical system, and cell, for detection and real-time imaging of concealed flaws, internal structures, and other similar matters, that are the natural intended subject of non-destructive and non-invasive testing of bodies, both inanimate and animate.

Thus, one object of this invention is to disclose an improved system, and an improved liquid crystal cell for use in an acousto-optic system, for non-destructive and non-invasive examination and testing of bodies, including concealed portions of said bodies, so as to provide a real-time image of the results of such testing.

Other objects of this invention will become apparent from the following description of the discoveries and in the appended claims.

SUMMARY OF THE INVENTION

It has been discovered that in addition to glass laminated cell covers, of acousto-optical detector cells as disclosed in my said co-pending application, cell covers which are not laminated (i.e., monolithic and/or of different materials) can be effectively used in acousto-optic cells and in acousto-optical systems. These new covers are readily fabricated into a cell and all exhibit excellent acoustic transmission. Furthermore, it has been found that cells which employ these covers have increased ultrasonic sensitivity and are relatively insensitive to a range of variations in the incident beam angle (i.e., angular variation from normal or perpendicular to the cell surface.)

Furthermore, it has been discovered that the performance of the cell can be enhanced by aligning the liquid crystal molecules obliquely, preferably at a small angle, to the incident ultrasonic beam. Such alignment permits the development or formation of the equivalent of a mechanical torque couple, that results in the liquid crystal molecule being more readily responsive, or reactant, to the ultrasonic energy, and thus more sensitive to incident, modified, ultrasonic energy that emerges from the body that is insonified.

It has been discovered that contrary to statements by Greguss, the effectiveness of acousto-optical cells have been further enhanced, by employing a biasing electric field as a means to align the nematic liquid crystals molecules relative to the vector of incident ultrasonic energy beam. Resolution and contrast can be further enhanced by use of a pulsed-ultrasonic beam and the synchronized use of selected frequencies for the electric field. Studies have also suggested that liquid crystal materials exhibit an optimum response at a particular frequency and that the temperature at which the cell is operated can affect cell sensitivity.

The cells disclosed herein are acoustically matched to the transducer frequency and surrounding sound transmitting medium, have high acoustic transmission, and are sensitive to small variations in received ultrasonic signals. Such cells are very effective to detect and display the image of a body which has been ultrasonically illuminated, or insonified.

BRIEF DESCRIPTION OF THE DRAWING

FIG. 1 is a diagrammatic view of a typical inspection system using reflective optics;

FIG. 2 is a diagrammatic view of a typical inspection system using transmissive optics;

FIG. 3 is a diagrammatic view showing the construction of a typical detector cell;

FIG. 7 is an illustration of the construction of a laminated glass cover for use in a detector cell of the type shown in FIGS. 1-4.

DESCRIPTION OF THE PREFERRED EMBODIMENT

Introduction

Figure 4:
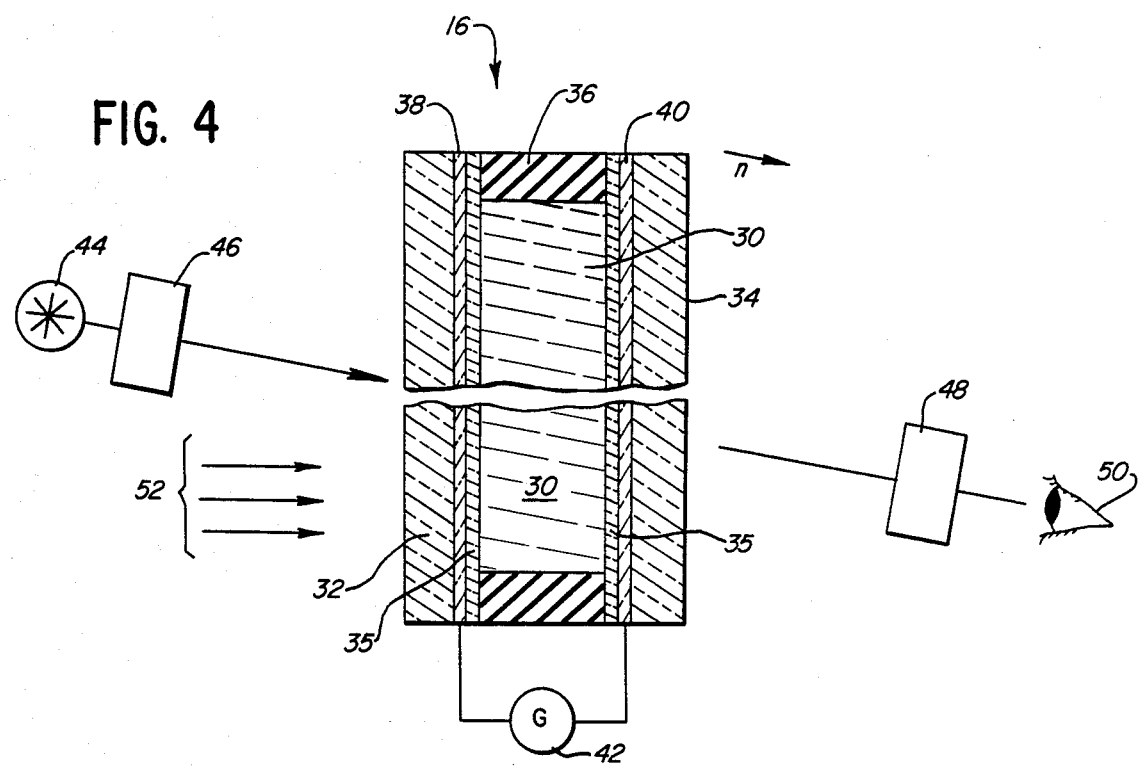
FIG. 4 is a diagrammatic view showing an improved detector cell constructed for electric field enhancement, and illustrating its relationship in a system that applies ultrasonics to the cell and how the same may be related to an optical system for viewing the display obtained on the liquid crystal material of the detector cell.

An ultrasonic inspection system which embodies the present invention is diagrammatically shown in FIGS. 1 and 2. In FIG. 1, a sending transducer 10 directs a vectored beam, 11, of ultrasonic energy through a body 12 which includes an internal defect 14. The ultrasonic energy, 15, exiting the insonified body carries with it information as to the internal structure and that energy is directed to the liquid crystal acouto-optical cell 16. A real-time image of the body is formed in the cell and is seen by the viewer 18 with the use of a reflective optical system which includes a collimated light source 20, polarizer 22, half-silvered mirror 24, for both reflection and transmission of light, as indicated, and a polarizer type analyzer 26. The transducer 10, body 12 and cell 16 are acoustically coupled to each other, usually by water, and in FIG. 1, the coupling is shown through a transparent water bath 28.

Another system which uses a transmission optical system is shown in FIG. 2 and has elements similar to those in FIG. 1. The principal difference is the inclusion in the water bath of a sonic reflector 25, which is optically transparent, and the deletion of the half-silvered mirror 24. It should be noted that acoustic lenses can be used, as needed, in either system to form the acoustic image of the body 12 on the cell 16.

In general, small (e.g., 0.2 mm) flaws 14 are located by using high frequency (e.g., 10 MHz) ultrasonic signals. However, absorption of ultrasonic energy is a function of the square of the frequency, and the use of high frequency signals can result in appreciable absorption of the ultrasonic radiation in the coupling medium, particularly where the signal path from the transducer 10 to detector cell 16 is long. In order to inspect for small flaws and to minimize signal absorption, reflective systems are used so that the ultrasonic signal path can be minimized by bringing the detector cell close to the test object. However, where the flaw is larger, and thus lower frequency signals can be used, transmission systems having longer signal paths can be advantageously employed.

The acoustic coupling needn't be through a bath, but may be effected through films or layers of water or silicone liquids.

THE CELL—IN GENERAL

Turning now to the cell 16, shown generally as in FIG. 3, such a cell includes a liquid crystal layer 30 which is encapsulated in a chamber, or space, defined between a pair of, spaced, parallel, covers or substrates 32 and 34, and with the chamber completed by a peripheral seal 36.

Protective layers, generally designated 32a and 34a, prevent reaction between the liquid crystal material 30, and the substrates 32 and 34. As suggested by the lining in FIG. 3, the liquid crystal molecules of the liquid crystal material 30 are homeotropically aligned, which means the alignment or average direction of the molecules, is perpendicular to the adjacent sides of the substrates 32 and 34. Alignment is designated by a "director," which is an arrow with the letter "n". By proper selection and use of cell positioning relative to the incident ultrasonic beam 15, and to the geometry, materials and some image enhancing techniques, the performance of the cell 16 can be matched to the ultrasonic frequency so as to optimize the image displayed on the cell. Each of these elements is discussed hereinafter.

The Cell Covers or Substrates

Effective cell covers, or substrates, must meet several criteria. First, they must be substantially acoustically transparent. The major factors which affect transparency are substrate thickness, incident ultrasonic beam angle, and acoustic impedance of the substrate. According to traditional ultrasonic theory, a substrate is substantially transparent to ultrasonic radiation when the incident ultrasonic energy is normal or perpendicular to the substrate, and when the thickness of the substrate is a multiple of the wavelength divided by two ($N\lambda/2$). However, this relationship does not hold true where the incident beam is oblique, or not normal, to the substrate. Therefore, to be useful, the covers should also exhibit acoustic transmission at various incident beam angles, which transmission is substantially equal to the transmission at normal incidence.

In order to maximize transparency and minimize reflections, the acoustic impedance of the covers should approximate that of the coupling medium, which is usually water. More specifically, the acoustic impedance of water is $1.509 \times 10^6$ Kg/m$^2$ sec., and the acoustic impedance of the substrates should be within an order of magnitude of that value. Effective substrates have been used where impedance is not greater than about $5.0 \times 10^6$ Kg/m$^2$ sec. However, it must be remembered that impedance is not the sole factor governing acoustic transparency, and thus other materials may be suitable depending upon cell geometry, beam angle, etc.

Next, the covers must be substantially rigid so as to maintain a uniform thickness for the liquid crystal layer. Furthermore, the ultrasonically active area of each cover (i.e. the portions of the covers exposed to the ultrasonic beam and which overlie the liquid crystal material) should be of a substantially uniform thickness to avoid geometric variations in the cover which could affect acoustic transmission therethrough. The covers should not chemically react with the liquid crystal material, as such will degrade image quality. In addition, at least one cover must be optically transparent so that the viewer may see images produced by the liquid crystal.

In practice, it is desirable to have acoustic transmission through each cell cover as great as possible and transmission of greater than about 85% has been found to be acceptable. Preferably, such transmission should be available at angles between about $+40°$ from normal. This assures a wide band of the cell sensitivity by minimizing energy losses in the covers and maximizing transmission of incident ultrasonic energy to the liquid crystal.

There are a number of materials and geometric configurations which meet the specified criteria.

As one example, the laminated covers as described in copending application, Ser. No. 232,247 meet the criteria. Other materials which I discovered meet the stated performance criteria includes: multi-ply glass laminates; graphite fiber/epoxy composites; and certain polymeric materials. The graphite fiber/epoxy composites are fabricated by standard techniques in which unidirectional graphite fiber/epoxy sheets are overlaid to give any desired orientation for the composite and then fused and cured to form the composite. Composites which have transverse fiber orientations, angular orientations and parallel orientations have been prepared. Stretched film or membrane covers can also meet the criteria, but may have deficiencies, as far as the frames or fixtures required to maintain rigidity in large sizes.

The acoustic transmission characteristics, of several suitable cover materials, as a function of the incidence angle of the ultrasonic vector, or beam, at various frequencies have been determined. The importance of the incidence angle is related to the problems in assuring normal or perpendicular alignment of a cell and transducer in actual use. Perfect normal alignment is very difficult to obtain and maintain. Thus, it is desirable to have uniform high transmission over a broad range of angles, so as to minimize or eliminate alignment problems between the beam and cell in actual use. Covers, or substrates, which are not angularly sensitive are the most useful. It has been determined that for a given thickness of a cover, acoustic transmission varies principally with acoustic frequency, beam angle, nature of the cover material, and cover construction.

Tests have been run on three-ply glass laminates as cell covers. Each ply was 0.0085 inch thick and the plies were adhesively bonded to each other. The tests were run at frequencies between 2.5 and 6.0 MHz and at incident beam angles between $-60$ and $+60$ degrees from normal which is designated as zero (0°). The tests indicate that at frequencies between 4.5 and 6.0 MHz there are irregular responses, which indicate that these three ply glass laminates may be difficult to use in that frequency range. On the other hand, the tests at 3.5 and 4.0 MHz show three broad plateaus, namely between: about $-40$ and $-15$ degrees; about $-10$ and $+10$ degrees; and about $+15$ and $+40$ degrees. Transmission in these ranges was greater than 85%. These experimental results suggest good wide operating ranges. The acoustic impedance of glass is $11.4 \times 10^6$ Kg/m$^2$ sec. A typical laminated glass cell construction 60 is shown in FIG. 7 where the cover 62 includes three glass plies 64, 66 and 68 which are bonded by the two adhesive plies 70 and 72. The other cover is designated as 74, the spacer as 76 and the liquid crystal material as 78.

Another series of tests, on a material for a cell cover, were run on a 0.031 inch thick polyester sheet, commercially identified as Homalite 100, sold by SGL Homalite, 11 Brookside Drive, Wilmington, Del. 19804. This material meets Mil Specs Mil. P. 77C, Class Gl. The tests were run at frequencies between 2.5 and 6.0 MHz. At all frequencies the response is relatively flat at incident beam angles of between about $-20$ and $+20$ degrees. The major deviation from a flat response is at incident angles (1) between $+30$ and $+40$ degrees; and (2) between $-30$ and $-40$ degrees. At incident beam angles beyond $+40°$, the response is also relatively flat. Based on the discovered and observed acoustic response, this material is very desirable and has transmission greater than 85%. Furthermore, this material is optically transparent. In the thickness used, the material is also substantially rigid for the intended purposes. The acoustic impedance of the material is $3.0 \times 10^6$ Kg/m$^2$ sec. Thus from almost every aspect, this polyester provides an excellent cover material.

Another material which has been found to be useful as a cell cover is a laminate constructed of plies of graphite fiber/epoxy composite. In such composites, the plies are parallel to each other, but the fibers may be at right angles to each other. These laminates are: substantially rigid for the intended purposes, chemically compatible with liquid crystal materials, and exhibit good acoustic transmission (i.e., greater than 85%), but are optically opaque. Both three-layer and four-layer composites were tested at frequencies between 2.5 and 6.0 MHz, and the composites exhibited similar properties. The average value of the acoustic impedance of this material across the fibers, is estimated to be $1.5 \times 10^6$ Kg/m$^2$ sec.

Test results on the three-ply graphite/epoxy composite used as a cell cover show that transmission at frequencies between 2.5 to 3.5 MHz is relatively flat between incident beam angles about $-20$ and $+20$ degrees, with transmission being the greater at 3.5 MHz. At frequencies between 4.5 and 5.5 MHz, there exists a narrower band for securing desired results using incident beam angles of about −10 to +10 degrees, in which there was a relatively flat response with transmission greater than 85%. However, outside of that range the response falls off and was considered to be not acceptable.

Four-layer graphite fiber/epoxy composites have also been tested. The most uniform and predictable of the results were at frequencies between 2.5 and 3.5 MHz and with incident beam angles in the range of between about +20°. Test results at greater frequencies showed very peaky and non-uniform results.

Very surprisingly good results have been obtained with graphite fiber/epoxy composites when the layers are arranged so that all fibers are unidirectionally aligned to each other. It has been found that the ultrasonic transmissive character, with such a layered cover was, at most frequencies investigated, in the order of 90% over a very wide band incident angle band of about +40°. When the composite is arranged so that the fibers are transverse to the plane in which the transducer is moved, there is a slight drop in transmission at about +10 and −10 degrees. However, when the composite is rotated 90° so that the fibers are parallel to the plane in which the transducer is moved, the dip or loss of transmission is moved from the +10° positions to the +40° positions. Thus, depending on the application and sensitivity required, a composite substrate can be oriented so that the fibers are in the transverse or parallel orientation with respect to the plane of the transducer. A two-layer graphite/epoxy cell cover, wherein the layers had the fibers therein arranged parallel, was found to be the most effective cell cover tested. The graphite fiber/epoxy composite also has the desired rigidity and chemical stability. The particular layers had about 40% graphite fibers and about 60% epoxy. It is believed that the fiber content of the layers can be varied over a very wide range and still provide an effective substrate.

The graphite fiber/epoxy material is well known for use in aerospace industry. It is available in uncured form on rolls of a sheet substrate. Sources include HERCULES CORP. of MAGNA, UTAH or NARMCO CORP. of COSTA MESA, CALIF.

In a cell, one of the cell covers, or substrates, could be opaque and could be fabricated from a parallel fiber, graphite fiber/epoxy composite, and the other cell cover could be optically transparent and fabricated from an appropriate polyester, or be of glass laminate construction.

Both the polyester and graphite/epoxy substrates are easy to fabricate and make into cells. The glass laminate is somewhat more difficult to fabricate, but has also been successfully made into cells.

Monolithic glass covers have also been tested but exhibit irregular ultrasonic transmission characteristics which make them usable only under very carefully controlled conditions. Another cell cover can be prepared from a stretched polyester membrane. However, those membranes require complex frames to maintain their rigidity and tend to relax.

From the foregoing, it is seen that I have discovered that materials for a cell are available which provide over 85% acoustic transmission, at sonic incidence onto a cell cover between angles of about ±40° from normal, and in some instances, achieved sonic transmission is greater than 90%. In addition, the materials are sufficiently rigid to assure uniform thickness of the liquid crystal layer over a wide range of cell sizes.

Rigidity of the cell cover is important, to assure providing a cell size-to-image size ratio that minimizes edge effects of the cell. In other words, the cell size must be sufficiently greater than the image size so as to preclude the image approaching the cell edges, which could cause some distortion in the image produced.

Preferably, the two spaced covers of the cell are selected to be substantially equally acoustically transparent, over their entire operative areas, so as to minimize internal reflection within the liquid crystal layer of the cell, and this is achieved, in one manner herein, by making operative portions of the covers substantially identical in thickness, material, and orientation relative to the liquid crystal layer of the cell.

With respect to chemical sensitivity between the covers and the liquid crystal material, glass and graphite/epoxy are quite inert. However, it is good practice to always provide a protective barrier layer, such as a silicone oxide layer, or film, such as 32a and 34a, or 35, at the cover/liquid crystal interfaces. Such barrier layers can be vacuum deposited, or sputtered, onto the substrates. Such a barrier layer has been successfully used with each of the substrate materials disclosed herein. These barrier layers have a thickness of about 200 Angstroms, which is much much less than $\lambda/4$, where $\lambda$ is the wave length of the ultrasonic energy.

As can be seen, once the frequency of the ultrasonic energy is determined, appropriate cell covers can be selected to maximize acoustic transmission over a wide range of sonic incidence angles and the appropriate optically opaque or transparent covers selected.

The Liquid Crystal Material

The liquid crystal material positioned between the substrate covers, is the sensor which produces therein the ultrasonic image. The image is produced by the interaction of the ultrasonic energy with the liquid crystal material to produce birefringence. This effect is referred to as the acousto-optic effect, or the field birefringent effect. This effect is usually viewed using the collimated light source and polarizer/analyzer combination whose orientation is adjusted for best viewing conditions.

In general, the cells are constructed so that the maximum amount of ultrasonic energy is transmitted through both cell covers so that the ultrasonic energy absorbed within the cell is minimized. Furthermore, the liquid crystal material is selected or manipulated to maximize its sensitivity to variations in the ultrasonic signal and to maximize its response to the ultrasonic frequency used.

A liquid crystal material includes elongated molecules which are generally aligned with respect to each other. Such materials are anisotropic (i.e., their properties are not the same in every direction). This property is demonstrated by the optical birefringence which permits viewing of the image. The particular liquid crystal material is selected on the bases of: its sensitivity to the ultrasonic energy and the frequency used, its ability to be aligned relative to the cell covers, and to be moved from that alignment and returned to the alignment. Nematic liquid crystal materials are preferably used, as they can be selectively aligned with respect to the cell cover. The liquid crystal layer of the cell may include a single pure nematic material or a mixture of nematics. One nematic crystal material that has been successfully used is commercially known as K-15, has the chemical name 4-cyano-4'n-pentylphenyl and the following chemical structure:

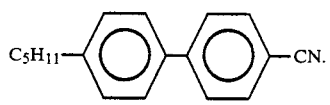

K-15 can be purchased from BDH Co., located in Poole, Dorset, England. Other nematics are commercially available. The nematics can be aligned normal to the cell substrates and have sufficient sensitivity. "Director" is a term used to designate the average or bulk alignment of the liquid crystal molecules. The "director" shown in FIGS. 3 and 4 of the drawings, includes the letter "n" and an arrow which points in the alignment direction. When the director is normal to the cell covers, the alignment is referred to as homeotropic.

It has also been found that mixtures of nematics can be employed to increase the sensitivity of the liquid crystal layer. In addition to pure nematics or nematic mixtures, a twisted nematic can be used. Twisted nematics are commonly used in electro-optic liquid crystal displays, for example, in digital watches. Twisted nematics are nematics to which approximately 0.03% by weight cholesteric liquid crystal material has been added, to provide a helical or twisted structure for the liquid crystal layer.

A nematic liquid crystal is a material whose phase changes with temperature from a crystalline phase to a nematic phase and then to an isotropic phase. It has been found that the sensitivity of nematics to ultrasonic energy is greatest at temperatures close to, but below the nematic/isotropic (N/I) phase transformation temperature. It has also been found that the response time of a cell (i.e., time to respond to the presence or absence of an ultrasonic signal) is improved, and appears to be most desirable, just below the N/I phase transformation temperature. Thus, in selecting a nematic liquid crystal, it is desirable to use a nematic liquid crystal having a N/I phase transformation temperature just above the operating temperature for the detector cell. The N/I temperature is a physical property of each nematic, but the N/I temperature of a liquid crystal material mixture can be adjusted by mixing nematics having different N/I temperatures. For K-15, the N/I transition is at about 35.3° C.

Furthermore, each particular liquid crystal material exhibits a maximum, or optimum, change in optical characteristics at one particular exciting frequency with the response being less at other frequencies. In other words, K-15 appears to be very responsive to ultrasonic energy and to be more responsive at 3.5 MHz than at any other frequency. Thus, in selecting a liquid crystal to be used in a given application, the frequency of maximum sensitivity should be considered.

Another consideration in selecting a liquid crystal is to employ a material which has a broad "non-streaming" band or region. In other words, the ultrasonic amplitude to be used must be maintained below the streaming point for the particular liquid crystal material.

It has also been discovered that streaming can be minimized by pulsing the ultrasonic beam. In other words, the ultrasonic transducer is cycled between operating and non-operating modes. Thus, energy is directed toward the cell for a very short period of time at which point the transducer is turned off and then turned back on again for a short period of time. An optical analogy is a stroboscopic light. It has been discovered that it is desirable to pulse the ultrasonic energy so as to reduce the amount of energy absorbed by the liquid crystal layer, and to thereby minimize the problem of streaming.

In order to maximize the sensitivity and response time in the pulsed mode, electric field enhancement may be used. In such a system, an electric field is applied to the cell in relation to the on and off modes of the ultrasonic beam. It has been found that sensitivity can be increased by applying an electric field of a first frequency, $f_1$, while the ultrasonic beam is on. The frequency is selected to orient the liquid crystals in a direction that is not normal to the cell covers, and thus aids the acoustic field in production of the image. This also aids in reducing the time period required to effect image forming in the detector cell, known as rise time.

Figure 5:
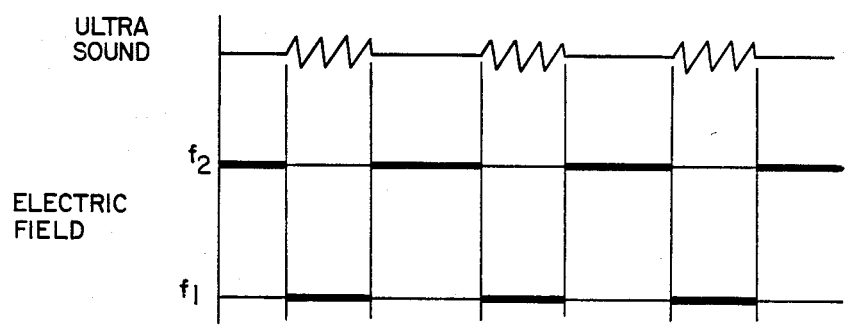
FIG. 5 is a diagram showing the use of selective electric field enhancement with pulsed ultrasonic energy.

It has also been found that the cell can be restored to its original condition by removing the first frequency field and applying a second electric field of a different frequency, $f_2$, when the ultrasonic beam is switched off. The second frequency is selected to restore the liquid crystal molecules to a position normal to the cell covers. The sequencing of applying these frequency fields is shown in FIG. 5, as related to the ultrasonic field.

More specifically, a 5 MHz ultrasonic signal can be pulsed for 50-100 microsecond duration with a few millisecond delay. The first frequency could be 5 KHz and the second 20 KHz.

Nematic liquid crystal materials usually exhibit a different dielectric constant in a direction parallel to the molecule's longitudinal axis than a direction transverse to the molecule's longitudinal axis. Thus, when the dielectric constant, $\epsilon$, in the parallel direction is represented by $\epsilon_{11}$, the subscript denoting "parallel", and in the transverse direction is represented by $\epsilon_\perp$, the subscript denoting "perpendicular", the differences may be represented as follows:

$$\Delta\epsilon = \epsilon_{11} - \epsilon_\perp > 0$$

$$\Delta\epsilon = \epsilon_\perp < 0$$

These relationships are important in determining how a liquid crystal will react to an electric field. For example, if $\Delta\epsilon > 0$, then molecules align parallel to a field, and if $\Delta\epsilon < 0$, they will align transverse to the field. For K-15, $\epsilon_{11} = 17.9$ and $\epsilon_\perp = 6.9$.

Furthermore, there exist liquid crystal materials in which the difference in dielectric constant changes from + to − with frequency. These are referred to as two-frequency materials, and exhibit the characteristic that below a particular frequency, $\Delta\epsilon$ will be greater than zero while above that frequency, $\Delta\epsilon$ will be less than zero. This property permits the use of a liquid crystal material such that the alignment of its director is controllable through selection of the frequency of electric field that is applied to the liquid crystal layer of the detecting cell. Two-frequency materials are particularly suitable for use in pulsed ultrasonic applications, to selectively produce parallel or perpendicular alignment.

A system for electric field enhancement is shown in FIG. 4, which illustrates diagrammatically the relationship of the elements of the system and details of the improved cell. Thus, FIG. 4 shows a light source 44 preferably collimated whose illumination is directed through a polarizer 46 toward the cell 16. Reference 52 represents the ultrasonic energy, or radiation, vectored in the direction of the arrows perpendicularly toward the surface of the cell, said cell being shown greatly enlarged in FIG. 4. In the illustration of FIG. 4, both the light source and ultrasonic energy are directed toward the cell from one side thereof. On the other side of the cell, there is a second polarizer, namely analyzer 48, and the observer or viewer 50 observing the effect of the ultrasonic energy upon the liquid crystal layer 30 of the cell 16. Reference "n" is the director, and it is shown parallel to, or aligned with the viewing axis, but it is oblique to the vector direction of the ultrasonic energy 52 and also to the outer surface of the covers 32 and 34 of the cell.

Referring specifically to the cell, shown greatly enlarged, the cell includes two spaced, parallel, substrates, 32 and 34; the liquid crystal material 30, such as K-15; the peripheral sealing spacer 36; and thin silicone oxide barrier layers 35 adjacent the liquid crystal 30, as shown. Between each of the barrier layers 35 and their respective adjacent substrates 32 and 34, there are provided thin film, transparent, electrodes, 38 and 40 whose thickness is much much less than $\lambda/4$. These electrodes are substantially co-extensive in area size with the substrates. The electrodes are electrically connected to a generator 42, which supplies low frequency AC to the electrodes. The low frequency AC, applied at a low voltage (i.e. up to 10 volts r.m.s.) to electrodes 38 and 40 prevents ion migration and maintains the desired alignment of liquid crystal molecules.

Before the cell 16 is assembled to the condition shown in FIG. 4, the substrates 32 and 34, each with its adjacent electrode and silicone oxide barrier layer applied thereto, has the exposed surface of the barrier layer rubbed with fine tissue paper or other material, unidirectionally for an ultimate purpose of providing a desired alignment effect on the molecules of the liquid crystal material 30, namely causing the molecules of the liquid crystal material to become oriented in a generally uniform attitude, which can, with application of an electric field, be moved between a homeotropic alignment that is substantially normal to the cell covers and an inclined alignment, such as parallel to a director, such as shown by "n" in FIG. 4. Before assembly of the cell, and after the rubbing, the rubbed surfaces are coated with a surfactant, such as lecithin, which is in contact with the liquid crystal material 30 in the assembled cell.

It is known to apply lecithin or other similar surfactant chemicals to surfaces in contact with liquid crystals, in order to initially align the liquid crystal molecules. The lecithin molecules are believed to align the liquid crystal molecules perpendicular to contact surfaces. Although lecithin or another surfactant could be used herein, the AC electric field is principally relied on for alignment.

In addition to the field acousto-optical effect described here, there are additional acousto-optical effects, such as guest/host, which can be used. Guest/host, which combines a nematic crystal as "host" and a dichroic dye as the "guest", employs a dye to make the image visible.

In connection with the liquid crystal layer, it has been found that the liquid crystal layer is preferably approximately 0.020 inches thick, the spacing between the two barrier layers 35, and should not be less than 0.015 inches thick. The reason is that in this thickness the surface effects of the substrates are minimized and the bulk of the liquid crystal can respond to the ultrasonic energy. While these thicknesses are preferred, it must be recognized that the ultrasonic frequency and cell cover construction will affect the choice of thickness of the liquid crystal layer, and may even permit use of thinner layers.

The structure of the cell shown in FIG. 4 is preferred for increasing the sensitivity of the cell by aligning the liquid crystal molecules obliquely to the entering ultrasonic beam 52. Thus, when the beam 52 is normal to the cell, the director "n" of the molecules should be inclined at a small angle (e.g., less than 10°) to the covers; or if the beam 52 is inclined at a small angle to the normal of the cell cover, then the director "n" of the molecules should not be parallel to the vector of the ultrasonic beam, but should be inclined to the beam and may be normal, or homeotropically aligned to the substrates. In either system the optical view axis should be substantially parallel to the molecular alignment as indicated by the director "n".

It has been discovered that the oblique liquid crystal director/ultrasonic beam alignment increases sensitivity, since the vector of the force of the ultrasonic beam is not directly aligned with the ends of the liquid crystal molecules in an axial direction, but rather is directed to strike the side of the molecule, to produce, or induce, a stress or strain effect, such as a bending, a tipping, or rotary motion of the liquid crystal molecules that will produce the desired birefringence. This effect, or action, can be also thought of as a torque couple, as that term is used in mechanics.

In order to assure a uniform reaction of the liquid crystal in the oblique alignment the substrates are first unidirectionally rubbed or chemically treated to produce an initial alignment. See, *F. J. Kahn, et. al.,* Journal of Applied Physics 1972.

Then a liquid crystal is selected in which $\Delta\epsilon<0$, and a slight electric field is applied by generator 42 to produce the oblique alignment of the liquid crystal relative to the plane of the substrate.

Referring to FIG. 4, the transmission optical system is shown preferably aligned with the director, "n", and includes the light source 44, polarizer 46, analyzer 48 and viewer 50. The ultrasonic energy 52 from the test object is shown at normal incidence to the cell. Normal incidence is preferred, as the substrate must follow the $\lambda/2$ rule, but non-normal or oblique incidence could also be used.

From the foregoing, it is seen that once the ultrasonic frequency is known and the cell covers have been selected, a suitable liquid crystal material can be selected which has the maximum sensitivity for that frequency or band. Then, if necesssary, electric field enhancement and pulsed ultrasonic signals can be used to further enhance the image, sensitivity, resolution and response time.

Cell Construction

The construction of each cell will vary depending upon the specific application or use to which the cell is placed.

For example, if the image on the liquid crystal is to be viewed using transmission optics (i.e., by light shining through the cell), then both cell covers must be acoustically and optically transparent. Both covers could be glass laminates or polyesters or one cover could be glass laminate and the other cover a polyester.

On the other hand if the optical system is to be reflective, then the cell cover on the object side will be acoustically transparent and optically opaque, with an optical mirror surface applied to the cover surface which interfaces with the liquid crystal. Such a cover on the object side could be an epoxy/graphite composite. The other cover should be optically transparent, such as glass laminate or polyester.

The following operational performance characteristics have been obtained using cells as described above.
Visual operating sensitivity—less than 300 microwatts/cm$^2$
Resolution—300 microns in a water bath using 5 MHz frequency
Response time—less than 1 second By using structures and systems as described herein, flaws in many substances have been detected. As an example, a visco elastic flaw, in the form of a square patch, sized $\frac{3}{8}'' \times \frac{3}{8}'' \times 0.001$ inch, embedded in a 16-ply epoxy/graphite composite that was $\frac{1}{8}$ inch thick, was successfully observed using a liquid crystal cell. The material examined was of the type which is now used in aerospace applications.

Figure 6:
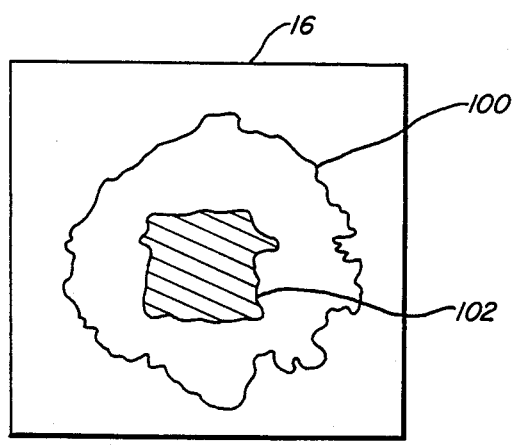
FIG. 6 is an illustration showing the real-time ultrasonic image of a concealed defect in a body, as shown on a liquid crystal.

FIG. 6 is a representation of the light illuminated liquid crystal cell 16, which exhibits thereon the acoustical image of an insonified test object and the flaw embedded in said test object. In the drawing the generally circular area 100 illustrates the insonified field image that appears on cell 16, and cross-hatched square 102, located centrally of the insonified field image 100, represents a typical appearance of a detected flaw, or defect, embedded in the graphite/epoxy material being examined.

The following table sets forth some of the cells which have been made and tested. These cells all use K-15 liquid crystal materials, were $2'' \times 2''$ in size, were tested at 3.5 MHz and 5.0 MHz and produced satisfactory images at various angles of the ultrasonic vector 52 to the outer surface of the cell cover. Where "polyester" is referred to, the material was "Homolite" as referred to hereinabove.

| Object - Side Cover | Liquid Crystal Viewer - Side Cover | Thickness |
| --- | --- | --- |
| .037 inch glass | .037 inch glass | .020 inch |
| .037 inch glass | .037 inch glass | .005–.010 |
| .015 inch graphite fiber/epoxy | .037 inch glass | .005–.010 |
| .032 inch polyester. | .032 inch polyester | " |
| .032 inch polyester. | .037 inch glass | " |
| .030 inch polymethyl methacrylate (Plexiglas) | .037 inch glass | " |
| 3-ply glass (.0085 inch plies) | 3-ply glass (.0085 inch plies) | " |

The Ultrasonic Transducer

The ultrasonic generators or transducers used herein are of the conventional piezoelectric type which when electrically excited produce pressure waves in a liquid medium. As is known, it is desirable to work with a uniform beam of the type which is present at the near field/far field transition.

The physical location of the near field/far field transition is governed by the ratio of the square of the radius, A, of the transducer face divided by the ultrasonic wave-length namely $A^2/\lambda$. In some situations the distance to the transition is so long as to be impractical. In order to bring a uniform field closer to the transducer, several options are available. One option is to use an array of transducers which will generate a uniform field close to the transducer faces. Another option is to use a focused transducer which focuses a uniform beam at a predetermined point. However, such transducers will require either scanning or the use of an array to effectively insonify the test object.

"Speckle" or spots associated with the image is not a significant problem with the device described herein. Furthermore, image quality problems that are usually associated with "speckle" are minimized by using a uniform ultrasonic beam or an incoherent field.

The transducers which have been used in this system preferably generate frequencies in the range of 1–10 MHz. A particular frequency within that range is selected, the frequency depending upon the specific application or use for the system. It has been found that the frequency range of 3–6 MHz may be the most practical. However it is anticipated that frequencies outside the range of 1–10 MHz may be used, again depending upon the particular application.

Typical transducers which can be used are available from Krautkramer & Branson, or Panametrics, in a 1 inch diameter and at frequencies of 1, 3.5, and 5 MHz.

The cells and systems disclosed herein have been tested for use in industrial settings. However, these cells and systems are also suitable for use in medical imaging.

The System

As can be appreciated from the foregoing, the effectiveness of the ultrasonic inspection system is related to a combination of factors. These factors include the frequency of the ultrasonic signal, the intensity of the ultrasonic signal, the acoustic matching of the detector cell to the surrounding medium, the acoustic impedance of the cell covers, and the sensitivity of the liquid crystal material to the ultrasonic signal. The particular application for which the system is to be used will dictate the frequency of the ultrasonic signal, which in turn will suggest the construction and materials for the detector cell substrates as well as the particular liquid crystal material to be used. The problem of image enhancement will depend upon the application since in some situations the image quality without electric field enhancement will be satisfactory, whereas in other situations, it will not.

Thus, from the foregoing it should be understood that the system, as a whole, functions and cooperates as a combination.

Other features can be added to the system depending upon the application. For example, if a permanent record is desired, a photographic system can record the image on the cell. If remote displays are desirable, a video camera and transmission system can be used to capture the image on the cell.

It will be appreciated that numerous changes and modifications can be made to the embodiment shown herein without departing from the spirit and scope of this invention.

What is claimed and desired to be secured by Letters Patent of the United States is:

1. An ultrasonic imaging system for use in non-destructively and non-invasively testing objects, which includes a source or beam of ultrasonic energy, a liquid crystal detector cell acoustically coupled to said beam for displaying a real-time image of a test object, and an optical viewing system for illuminating the image on the cell, wherein said cell includes a pair of closely spaced and parallel covers, the ultrasonically active area of each being of a substantially uniform thickness, said covers encasing a nematic liquid crystal material whose alignment is indicated by a director, said material exhibiting field birefringence in response to acoustic energy, said cell being matched to the frequency of the ultrasonic energy, by each of said covers being substantially acoustically transparent to ultrasonic beams incident on said covers at normal and oblique angles and the liquid crystal alignment as indicated by the director being oblique relative to the covers, and said cell exhibiting high sensitivity and high image resolution.

2. A system as in claim 1, wherein the optical viewing axis is substantially parallel to the liquid crystal alignment.

3. A system as in claim 2, wherein the liquid crystal image is enhanced by electric field alignment and wherein the liquid crystal material exhibits a different dielectric constant in a direction parallel to the longitudinal axis of the molecule than in a direction perpendicular to the longitudinal axis of the molecule.

4. A system as in claim 3, wherein the difference in dielectric constants is less than zero and the electric field causes said oblique alignment.

5. A liquid crystal detector cell for use in an ultrasonic imaging system to non-destructively and non-invasively test objects and produce a real-time image thereof, wherein said cell includes a pair of closely spaced and parallel covers, the ultrasonically active area of each of which is of substantially uniform thickness, said covers encasing a nematic liquid crystal material whose alignment is indicated by a director, said material exhibiting field birefringence in response to acoustic energy, said cell being matched to the frequency of the ultrasonic energy, by said covers being substantially acoustically transparent to ultrasonic beams incident on said covers at normal and oblique angles and wherein the liquid crystal alignment as indicated by the director being oblique relative to the cover and said cell exhibiting high sensitivity and high image resolution.

6. A cell as in claim 5, wherein the liquid crystal image is enhanced by electric field alignment and wherein the liquid crystal material exhibits a different dielectric constant in a direction parallel to the longitudinal axis of the molecule than in a direction perpendicular to the longitudinal axis of the molecule.

7. A cell as in claim 6, wherein the difference in dielectric constants is less than zero and the electric field causes said oblique alignment.

8. A cell as in claim 5, wherein the liquid crystal image is enhanced by electric field alignment, the liquid crystal material exhibiting a different dielectric constant in a direction parallel to the longitudinal axis of the molecule than in a direction perpendicular to the longitudinal axis of the molecule, and the difference in dielectric constants is less than zero and the electric field causes a slight oblique alignment.

9. An ultrasonic imaging system for use in non-destructively and non-invasively testing objects, which includes a source or beam of ultrasonic energy, a liquid crystal detector cell acoustically coupled to said beam for displaying a real-time image of a test object, and an optical viewing system for illuminating the image on the cell, wherein said cell includes a pair of closely spaced and parallel covers, the ultrasonically active area of each being of a substantially uniform thickness, said covers encasing a nematic liquid crystal material whose alignment is indicated by a director, said material exhibiting field birefringence in response to acoustic energy, said cell being matched to the frequency of the ultrasonic energy, by each of said covers being substantially acoustically transparent to ultrasonic beams incident on said covers at normal and oblique angles, the liquid crystal material being selectively aligned, said cell exhibiting high sensitivity and high image resolution, and one of said covers comprising a multi-layer graphite fiber/epoxy composite.

10. A system as in claim 9, wherein the graphite fibers in the composite are substantially parallel to each other.

11. A system as in claim 9, wherein the graphite fibers are at substantially right angles to each other.

12. A system as in claim 9, wherein each of said cell covers includes a protective layer to prevent chemical reaction between the liquid crystal material and the cell cover.

13. A liquid crystal detector cell for use in an ultrasonic imaging system to non-destructively and non-invasively test objects and produce a real-time image thereof, wherein said cell includes a pair of closely spaced and parallel covers, the ultrasonically active area of each of which is of substantially uniform thickness, said covers encasing a nematic liquid crystal material whose alignment is indicated by a director, said material exhibiting field birefringence in response to acoustic energy, said cell being matched to the frequency of the ultrasonic energy, by said covers being substantially acoustically transparent to ultrasonic beams incident on said covers at normal and oblique angles, the liquid crystal material being selectively aligned, said cell exhibiting high sensitivity and high image resolution, and one of said covers comprising a multi-layer graphite fiber/epoxy composite.

14. A cell as in claim 13, wherein the graphite fibers in the composite are substantially parallel to each other.

15. A cell as in claim 13, wherein the graphite fibers in the composite are at substantially right angles to each other.

16. A cell as in claim 13, wherein each of said cell covers includes a protective layer to prevent chemical reaction between the liquid crystal material and the cell cover.

17. An ultrasonic imaging system for use in non-destructively and non-invasively testing objects, which includes a source or beam of ultrasonic energy, a liquid crystal detector cell acoustically coupled to said beam for displaying a real-time image of a test object, and an optical viewing system for illuminating the image on the cell, wherein said cell includes a pair of closely spaced and parallel covers, the ultrasonically active area of each being of a substantially uniform thickness, said covers encasing a nematic liquid crystal material whose alignment is indicated by a director, said material exhibiting field birefringence in response to acoustic energy, said cell being matched to the frequency of the ultrasonic energy, by each of said covers being substantially acoustically transparent to ultrasonic beams incident on said covers at normal and oblique angles, said liquid crystal material being selectively aligned, said cell exhibiting high sensitivity and high image resolution, and wherein at least one of said cell covers is of a polymeric material and there is provided on said cover a protective barrier layer to prevent chemical reaction between the liquid crystal material and the cell cover.

18. A system as in claim 17, wherein said polymer is a polyester.

19. A system as in claim 17, wherein said polymer is substantially rigid so as to maintain a uniform spacing between said cover surfaces and thereby maintain the liquid crystal layer of a uniform thickness.

20. A liquid crystal detector cell for use in an ultrasonic imaging system to non-destructively and non-invasively test objects and produce a real-time image thereof, wherein said cell includes a pair of closely spaced and parallel acoustically transparent covers, the ultrasonically active area of each of which is of substantially uniform thickness and which encase a nematic liquid crystal material whose alignment is indicated by a director, said material exhibiting field birefringence in response to acoustic energy, said cell being matched to the frequency of the ultrasonic energy, by said covers being substantially acoustically transparent to ultrasonic beams incident on said covers at normal and oblique angles and wherein the liquid crystal material is selectively aligned, said cell exhibiting high sensitivity and high image resolution, wherein at least one of said cell covers is of a polymeric material and there is provided on said cover a protective layer to prevent chemical reaction between the liquid crystal material and the cell cover.

21. A cell as in claim 20, wherein said polymer is a polyester.

22. A cell as in claim 20, wherein said polymeric is substantially rigid so as to maintain a uniform spacing between said cover surfaces and thereby maintain the liquid crystal layer of a uniform thickness.

23. An ultrasonic imaging system for use in non-destructively and non-invasively testing objects, which includes a source or beam of ultrasonic energy, a liquid crystal detector cell acoustically coupled to said beam for displaying a real-time image of a test object, and an optical viewing system for illuminating the image on the cell, wherein said cell includes a pair of closely spaced and parallel covers, the ultrasonically active area of each being of a substantially uniform thickness, said covers encasing a nematic liquid crystal material whose alignment is indicated by a director, said material exhibiting field birefringence in response to acoustic energy, said cell being matched to the frequency of the ultrasonic energy, by each of said covers being substantially acoustically transparent to ultrasonic beams incident on said covers at normal and oblique angles, the liquid crystal material being selectively aligned and said cell exhibiting high sensitivity and high image resolution, and wherein said liquid crystal exhibits a nematic/isotropic phase transition temperature just above the ambient temperature at which said system is expected to operate.

24. A liquid crystal detector cell for use in an ultrasonic imaging system to non-destructively and non-invasively test objects and produce a real-time image thereof, wherein said cell includes a pair of closely-spaced and parallel covers, the ultrasonically active area of each of which is of substantially uniform thickness, said covers encasing a nematic liquid crystal material whose alignment is indicated by a director, said material exhibiting field birefringence in response to acoustic energy, said cell being matched to the frequency of the ultrasonic energy, by said covers being substantially acoustically transparent to ultrasonic beams incident on said covers at normal and oblique angles, the liquid crystal material being selectively aligned, said cell exhibiting high sensitivity and high image resolution, and wherein said liquid crystal exhibits a nematic/isotropic phase transition temperature just above the ambient temperature at which said cell is expected to operate.

25. An ultrasonic imaging system for use in non-destructively and non-invasively testing objects, which includes a source or beam of ultrasonic energy, a liquid crystal detector cell acoustically coupled to said beam for displaying a real-time image of a test object, and an optical viewing system for illuminating the image on the cell, wherein said cell includes a pair of closely spaced and parallel covers, the ultrasonically active area of each being of a substantially uniform thickness, said covers encasing a nematic liquid crystal material whose alignment is indicated by a director, said material exhibiting field birefringence in response to acoustic energy, said cell being matched to the frequency of the ultrasonic energy, by each of said covers being substantially acoustically transparent to ultrasonic beams incident on said covers at normal and oblique angles, the liquid crystal material being selectively aligned, said cell exhibiting high sensitivity and high image resolution, and wherein the liquid crystal image is enhanced by electric field alignment and the liquid crystal material exhibits a different dielectric constant in a direction parallel to the longitudinal axis of the molecule than in a direction perpendicular to the longitudinal axis of the molecule, and said dielectric constant changes with frequency, and wherein said ultrasonic source emits pulses of ultrasonic energy in a pulse-on mode and is quiescent in the pulse-off mode, and wherein an electric field of a first frequency is applied to align the liquid crystal molecules in a direction perpendicular to the electric field when the ultrasonic generator is in the pulse-on mode and a second electric field at a second frequency is applied to align the liquid crystal molecules in a direction parallel to the electric field when the ultrasonic generator is in the pulse-off mode.

26. A liquid crystal detector cell for use in an ultrasonic imaging system to non-destructively and non-invasively test objects and produce a real-time image thereof, wherein said cell includes a pair of closely spaced and parallel covers, the ultrasonically active area of each of which is of substantially uniform thickness, said covers encasing a nematic liquid crystal material whose alignment is indicated by a director, said material exhibiting field birefringence in response to acoustic energy, said cell being matched to the frequency of the ultrasonic energy, by said covers being substantially acoustically transparent to ultrasonic beams incident on said covers at normal and oblique angles, the liquid crystal material being selectively aligned, said cell exhibiting high sensitivity and high image resolution, wherein the liquid crystal image is enhanced by electric field alignment and the liquid crystal material exhibiting a different dielectric constant in a direction parallel to the longitudinal axis of the molecule than in a direction perpendicular to the longitudinal axis of the molecule, and wherein said dielectric constant changes with frequency and wherein an electric field of a first frequency is applied to align the liquid crystal molecules in a direction perpendicular to the electric field when an ultrasonic source is on and a second electric field at a second frequency is applied to align the liquid crystal molecules in a direction parallel to the electric field when the ultrasonic field is off.

27. An ultrasonic imaging system for use in non-destructively and non-invasively testing objects, which includes a source or beam of ultrasonic energy, a liquid crystal detector cell acoustically coupled to said beam for displaying a real-time image of a test object, and an optical viewing system for illuminating the image on the cell, wherein said cell includes a pair of closely spaced and parallel covers, the ultrasonically active area of each being of a substantially uniform thickness, said cover encasing a nematic liquid crystal material whose alignment is indicated by a director, said material exhibiting field birefringence in response to acoustic energy, said cell being matched to the frequency of the ultrasonic energy, by each of said covers being substantially acoustically transparent to ultrasonic beams incident on said covers at normal and oblique angles, the liquid crystal material being selectively aligned, said cell exhibiting high sensitivity and high image resolution, and wherein said liquid crystal material exhibits its maximum frequency response at the ultrasonic frequency selected for imaging.

28. A liquid crystal detector cell for use in an ultrasonic imaging system to non-destructively and non-invasively test objects and produce a real-time image thereof, wherein said cell includes a pair of acoustically transmissive covers, the ultrasonically active area of each of which is of substantially uniform thickness and which encase a nematic liquid crystal material whose alignment is indicated by a director, said material exhibiting birefringence in response to acoustic energy, said cell being matched to the frequency of the ultrasonic energy, by said covers being substantially acoustically transparent to ultrasonic beams incident on said covers at normal and oblique angles, the liquid crystal material being selectively aligned, said cell exhibiting high sensitivity and high image resolution and wherein the liquid crystal material exhibits its maximum frequency response at the ultrasonic frequency selected for imaging.

29. A system as in claim 1, 9 or 17, wherein the liquid crystal exhibits a nematic/isotropic phase transition temperature just above the ambient temperature at which said system is expected to operate.

30. A cell as in claim 5, 13 or 20, wherein the liquid crystal exhibits a nematic/isotropic phase transition temperature just above the ambient temperature at which said system is expected to operate.

31. A system as in claim 1, 9 or 17, wherein said liquid crystal material exhibits its maximum frequency response at the ultrasonic frequency selected for imaging.

32. A cell as in claim 5, 13 or 20, wherein said liquid crystal material exhibits its maximum frequency response at the ultrasonic frequency selected for imaging.

33. A system as in claim 9 or 17, wherein said liquid crystal material is obliquely aligned relative to the covers.

34. A cell as in claim 13 or 20, wherein the liquid crystal material is obliquely aligned relative to the cell cover.

35. A system as in claim 9 or 17, wherein the liquid crystal image is enhanced by electric field alignment and the liquid crystal material exhibits a different dielectric constant in a direction parallel to the longitudinal axis of the molecule than in a direction perpendicular to the longitudinal axis of the molecule, and said dielectric constant changes with frequency, and wherein said ultrasonic source emits pulses of ultrasonic energy in a pulse-on mode and is quiescent in the pulse-off mode, and wherein an electric field of a first frequency is applied to align the liquid crystal molecules in a direction perpendicular to the electric field when the ultrasonic generator is in the pulse-on mode and a second electric field at a second frequency is applied to align the liquid crystal molecules in a direction parallel to the electric field when the ultrasonic generator is in the pulse-off mode.

36. A cell as in claim 13 or 20, wherein the liquid crystal image is enhanced by electric field alignment and the liquid crystal material exhibits a different dielectric constant in a direction parallel to the longitudinal axis of the molecule than in a direction perpendicular to the longitudinal axis of the molecule, and said dielectric constant changes with frequency, and wherein said ultrasonic source emits pulses of ultrasonic energy in a pulse-on mode and is quiescent in the pulse-off mode, and wherein an electric field of a first frequency is applied to align the liquid crystal molecules in a direction perpendicular to the electric field when the ultrasonic generator is in the pulse-on mode and a second electric field at a second frequency is applied to align the liquid crystal molecules in a direction parallel to the electric field when the ultrasonic generator is in the pulse-off mode.

37. A system as in claim 9 or 17, wherein the ultrasonic beam and the liquid crystal alignment as indicated by the director are oblique to each other.

38. A system as in claim 9 or 17, wherein the nematic liquid crystal is homeotropically aligned.

39. A system as in claim 1, 9 or 17, wherein the acoustic impedance of each of said cell covers is of the same order of magnitude as the coupling medium.

40. A system as in claim 9 or 17, wherein the optical viewing axis is substantially parallel to the liquid crystal director.

41. A system as in claim 1, 9 or 17, wherein the acoustic transmission through each cover of said cell is at least 85 percent at any frequency between 1 and 10 MHz.

42. A system as in claim 1, 9 or 17, wherein at least one of said covers is optically transparent.

43. A system as in claim 42, wherein the optical system is of the reflective type and there is only one optically transparent cover and said optically transparent cover is positioned toward the viewing system.

44. A system as in claim 1 or 17, wherein both of said covers are optically transparent.

45. A system as in claim 44, wherein said optical system is of a transmission type whereby light is directed through the cell so as to permit viewing of the image.

46. A system as in claim 1, 9 or 17, wherein each of said cell covers is chemically inert with respect to the liquid crystal material.

47. A system as in claim 1, 9 or 17, wherein at least one of said cell covers is a three-ply glass laminate and wherein the thickness of each glass ply is about 0.0085 inch.

48. A system as in claim 1 or 9, wherein each of said covers is substantially rigid so as to maintain a uniform spacing between said cover surfaces and thereby maintain the liquid crystal layer of a uniform thickness.

49. A system as in claim 9 or 17, wherein said nematic liquid crystal molecules are aligned substantially normal to the cell covers.

50. A system as in claim 1, 9 or 17, wherein said liquid crystal material is a substantially pure nematic.

51. A liquid crystal material as in claim 1, 9 or 17, wherein said liquid crystal is a mixture of substantially pure nematics.

52. A system as in claim 9 or 17, wherein said liquid crystal is a mixture of nematic and approximately 0.03 percent by weight cholesteric added thereto.

53. A system as in claim 1, 9 or 17, wherein said liquid crystal material maintains its biased alignment and does not stream at the ultrasonic intensity employed by said system.

54. A system as in claim 1, 9 or 17, wherein said liquid crystal material is at least 0.015 inch thick.

55. A system as in claim 9 or 17, wherein the liquid crystal image is enhanced by electric field alignment and wherein the liquid crystal material exhibits a different dielectric constant in a direction parallel to the longitudinal axis of the molecule than in a direction perpendicular to the longitudinal axis of the molecule.

56. A system as in claim 55 wherein a thin film electrode is applied to each of said cell covers and each of said electrodes is connected to an AC generator for applying an electric field to said liquid crystal material.

57. A system as in claim 1, 9 or 17, wherein a uniform ultrasonic beam is generated and said object to be inspected is illuminated by the uniform beam.

58. A system as in claim 57, wherein said ultrasonic source is unfocused coherent sound source and said uniform illumination occurs at the near field/far field transition.

59. A system as in claim 57, wherein said ultrasonic transducer is focused transducer which focuses a uniform beam on a test object.

60. A system as in claim 57, wherein said uniform beam is obtained using an array of transducers.

61. A system as in claim 57, wherein the frequency of said transducer is between 1 and 10 MHz.

62. A system as in claim 57, wherein said ultrasonic transducer generates an incoherent ultrasonic beam.

63. A cell as in claim 5, 13 or 20, wherein the acoustic transmission through each cover of said cell is at least 85 percent at frequencies between 1 and 10 MHz.

64. A cell as in claim 5, 13 or 20, wherein at least one of said covers is optically transparent.

65. A cell as in claim 64, wherein the optical system is of the reflective type and there is only one optically transparent cover and said optically transparent cover is positioned toward the viewing system.

66. A cell as in claim 5 or 20, wherein both of said covers are optically transparent.

67. A cell as in claim 5, 13 or 20, wherein each of said cell covers is chemically inert with respect to the liquid crystal material.

68. A cell as in claim 5, 13 or 20, wherein at least one of said cell covers is a three-ply glass laminate and wherein the thickness of each glass ply is about 0.0085 inch.

69. A cell as in claim 5 or 13, wherein each of said covers is substantially rigid so as to maintain a uniform spacing between said cover surfaces and thereby maintain the liquid crystal layer of a uniform thickness.

70. A cell as in claim 13 or 20, wherein said nematic liquid crystal molecules are aligned substantially normal to the cell covers.

71. A cell as in claim 5, 13 or 20, wherein said liquid crystal material is a substantially pure nematic.

72. A cell as in claim 5, 13 or 20, wherein said liquid crystal is a mixture of substantially pure nematics.

73. A cell as in claim 13 or 20, wherein said liquid crystal is a mixture of nematic and approximately 0.03 percent by weight cholesteric added thereto.

74. A cell as in claim 5, 13 or 20, wherein said liquid crystal material maintains its biased alignment and does not stream at the ultrasonic intensity employed by said system.

75. A cell as in claim 5, 13, or 20, wherein said liquid crystal material is at least 0.015 inch thick.

76. A cell as in claim 13 or 20, wherein the liquid crystal image is enhanced by electric field alignment and wherein the liquid crystal material exhibits a different dielectric constant in a direction parallel to the longitudinal axis of the molecule than in a direction perpendicular to the longitudinal axis of the molecule.

77. A cell as in claim 76, wherein a thin film electrode is applied to each of said cell covers and each of said electrodes is connected to an AC generator for applying an electric field to said liquid crystal material.

* * * * *

UNITED STATES PATENT AND TRADEMARK OFFICE
CERTIFICATE OF CORRECTION

PATENT NO. : 4,506,550
DATED : March 26, 1985
INVENTOR(S) : Jaswinder S. Sandhu

It is certified that error appears in the above—identified patent and that said Letters Patent is hereby corrected as shown below:

Column 5, line 38, change "+40°" to -- $\pm 40°$ --.

Column 6, line 40, change "+40°" to -- $\pm 40°$ --.

Column 7, line 11, change "+20°" to -- $\pm 20°$ --.

Column 7, line 20, change "+40°" to -- $\pm 40°$ --.

Column 7, line 26, change "+10°" to -- $\pm 10°$ --.

Column 7, line 27, change "+40°" to -- $\pm 40°$ --.

Column 10, line 44, change "$\Delta \epsilon = \epsilon_\perp < 0$" to -- $\Delta \epsilon = \epsilon_\perp - \epsilon_\parallel < 0$ --.

*Signed and Sealed this*

*Twentieth* Day of *August 1985*

[SEAL]

Attest:

DONALD J. QUIGG

*Attesting Officer*   *Acting Commissioner of Patents and Trademarks*